(12) United States Patent
Nakano et al.

(10) Patent No.: US 11,175,196 B2
(45) Date of Patent: Nov. 16, 2021

(54) FLUID PRESSURE DETECTION DEVICE

(71) Applicant: TDK Corporation, Tokyo (JP)

(72) Inventors: Mutsuko Nakano, Tokyo (JP); Tomohiro Moriki, Tokyo (JP)

(73) Assignee: TDK Corporation, Tokyo (JP)

(*) Notice: Subject to any disclaimer, the term of this patent is extended or adjusted under 35 U.S.C. 154(b) by 137 days.

(21) Appl. No.: 16/498,734

(22) PCT Filed: Mar. 6, 2018

(86) PCT No.: PCT/JP2018/008665
§ 371 (c)(1),
(2) Date: Sep. 27, 2019

(87) PCT Pub. No.: WO2018/180289
PCT Pub. Date: Oct. 4, 2018

(65) Prior Publication Data
US 2020/0340876 A1    Oct. 29, 2020

(30) Foreign Application Priority Data
Mar. 29, 2017  (JP) .............................. JP2017-066169

(51) Int. Cl.
*G01L 9/08*         (2006.01)
(52) U.S. Cl.
CPC ...................................... *G01L 9/08* (2013.01)
(58) Field of Classification Search
CPC ..... G01L 9/08; G01L 7/00; G01L 9/06; A61B 5/021; A61B 5/022; A61B 5/02216
See application file for complete search history.

(56) References Cited

U.S. PATENT DOCUMENTS

| | | | | |
|---|---|---|---|---|
| 5,033,471 A | * | 7/1991 | Yokoe | A61B 5/022 600/494 |
| 2003/0009105 A1 | | 1/2003 | Lee et al. | |
| 2007/0000333 A1 | | 1/2007 | Brugger et al. | |
| 2007/0152679 A1 | * | 7/2007 | Kurtz | G01L 9/0052 324/610 |
| 2007/0287923 A1 | * | 12/2007 | Adkins | A61B 5/02405 600/485 |
| 2015/0238677 A1 | | 8/2015 | Akita et al. | |

FOREIGN PATENT DOCUMENTS

| | | |
|---|---|---|
| JP | 2002-224064 A | 8/2002 |
| JP | 5899308 B2 | 4/2016 |

OTHER PUBLICATIONS

International Search Report of International Application No. PCT/JP2018/008665, dated Jun. 5, 2018.

* cited by examiner

*Primary Examiner* — Benjamin R Schmitt
(74) *Attorney, Agent, or Firm* — Leydig, Voit & Mayer Ltd.; John Augustyn (57) ABSTRACT

A fluid pressure detection device capable of accurately detecting a pressure change of a fluid flowing inside a tube includes a substrate, and piezoelectric elements on the top surface of the substrate. The substrate is substantially rectangular in shape. The piezoelectric elements are arranged along the longitudinal direction of the substrate with long sides of each of the piezoelectric elements substantially perpendicular to the long side of the substrate. The substrate has slits on both sides of each of the piezoelectric elements in the longitudinal direction of the substrate. When detecting the pressure, the tube is deformed with a bottom surface of the substrate.

6 Claims, 9 Drawing Sheets

| Subject No. | 1 | 2 | 3 | 4 | 5 | 6 | 7 | 8 |
|---|---|---|---|---|---|---|---|---|
| fixing with tape | 8.0 | 5.5 | 8.8 | 3.3 | 2.6 | ~ | 3.4 | ~ |
| 40mmHg | 5.9 | 8.9 | 24.5 | 8.9 | 3.3 | 2.0 | 9.5 | 2.2 |
| 60mmHg | 13.3 | 19.2 | 38.2 | 40.2 | 8.8 | 6.4 | 8.3 | 7.4 |
| 80mmHg | 18.9 | 74.1 | 63.5 | 76.0 | 9.2 | 11.4 | 12.9 | 26.4 |
| 100mmHg | 57.4 | 64.2 | 65.2 | 77.1 | 20.2 | 42.0 | 21.8 | 38.2 |
| 120mmHg | 52.2 | 13.5 | 14.0 | 17.4 | 21.9 | 46.5 | 16.7 | 34.1 |

Unit[mV]

FLUID PRESSURE DETECTION DEVICE

TECHNICAL FIELD

The present invention relates to a fluid pressure detection device which detects pressure of a fluid flowing inside a tube.

BACKGROUND ART

For example, the heart is a pump in life which circulates blood throughout a whole body when four parts called "right atrium", "right ventricle", "left atrium" and "left ventricle" move at the same time. When these parts are moving regularly with a constant rhythm, it can be said that normal "beating" is going on. A word "pulsation" and not "beating" is used for what passes through the inside of a tube such as a blood vessel or piping, and pulsation occurs in the case of a positive displacement reciprocating pump. The pulse waveform is the waveform of artery inner pressure, and there is proposed a method of detecting this waveform of inner pressure from a body surface by using a piezoelectric ceramic or piezoelectric polymer resin.

The Patent Document 1 below relates to a broadband sensor and discloses constitution that the sensor comprises an insulating substrate, a piezoelectric element mounted to the surface of the insulating substrate and a cylindrical member installed to surround the piezoelectric element. By bringing an opening on a side opposite to the insulating substrate of the cylindrical member into contact with a body surface to form an airtight cavity in the inside of the cylindrical member, a pulse wave transmitted from a blood vessel below the body surface is detected as a change in air pressure in the cavity with the piezoelectric element.

PRIOR ART DOCUMENT

Patent Document

[Patent Document 1] Japanese Patent No. 5899308

SUMMARY OF THE INVENTION

Problem to be Solved by the Invention

When detecting pressure of fluid flowing inside the tube by a fluid pressure detection device using a piezoelectric element, it is important to align the piezoelectric element and the tube, but there is a case where high-precision positioning is difficult. In the case of a blood vessel for example, a mounting position is restricted by surrounding organization, thus it was difficult to accurately detect pressure changes.

It is an object of the present invention which was made in view of this situation to provide a fluid pressure detection device which can accurately detect from outside of a tube a pressure change of a fluid flowing inside the tube.

Means for Solving the Problem

One embodiment of the present invention relates to a fluid pressure detection device for detecting pressure of a fluid flowing inside a tube. The fluid pressure detection device includes:
a substrate; and
a plurality of piezoelectric elements on one surface of the substrate, wherein the tube is deformed with the other surface of the substrate.

The fluid pressure detection device may include a pressing member for pressing the substrate from the one surface side to press the other surface of the substrate against the tube.

The pressing member may apply a pressure of not less than 40 mmHg from the one surface side of the substrate.

The substrate may be substantially a rectangle. The piezoelectric elements may be arranged along the longitudinal direction of the substrate with long sides of each of the piezoelectric elements being substantially vertical to the long side of the substrate.

The long side of the substrate may be substantially parallel to the extending direction of the tube.

The substrate may have slits on both sides of each of the piezoelectric elements in the longitudinal direction of the substrate.

It is to be noted that any arbitrary combination of the above-described structural components as well as the expressions according to the present invention changed among a system and so forth are all effective as and encompassed by the present aspects.

Effect of the Invention

According to the present invention, there can be provided a fluid pressure detection device which can accurately detect from outside of a tube a pressure change of a fluid flowing inside the tube.

BRIEF DESCRIPTION OF DRAWINGS

FIG. 17 is a schematic diagram showing that the fluid pressure detection device 1 is pressed against the tube 7 through human skin gel 7a.

FIG. 22A and FIG. 22B are schematic sectional views of a measuring instrument used in first to third measurements, wherein

FIG. 26A and FIG. 26B are plane views of the substrate 10 and the piezoelectric element 20 of a fluid pressure detection device according to a second reference example of the present invention, wherein

FIG. 27A to FIG. 27C are perspective views of a support body 30 in the second reference example, wherein

FIG. 31A and FIG. 31B are planee views of the substrate 10 and the piezoelectric elements 20 of a fluid pressure detection device according to an embodiment of the present invention, wherein

FIG. 32A and FIG. 32B are graphs showing the relationship between the displacement against the tube 7 and standardized sensitivity in the fluid pressure detection device of the embodiment, wherein

FIG. 33A and FIG. 33B are graphs showing the relationship between the displacement of the tube 7 and sensitivity change rate in the fluid pressure detection device of the embodiment, wherein

FIG. 35A and FIG. 35B are graphs showing the relationship between the angle deviation against the tube 7 and standardized sensitivity in the fluid pressure detection device of the embodiment, wherein

FIG. 36A and FIG. 36B are graphs showing the relationship between the angle deviation against the tube 7 and sensitivity change rate in the fluid pressure detection device of the embodiment, wherein

EMBODIMENT FOR CARRYING OUT THE INVENTION

Preferred embodiments of the present invention will now be described in detail with reference to the drawings. The same or equivalent constituent parts, members, etc., shown in the drawings are designated by the same reference numerals and will not be repeatedly described as appropriate. The embodiments are not intended to limit the invention but are mere exemplifications, and all features or combinations thereof described in the embodiments do not necessarily represent the intrinsic natures of the invention.

First Reference Example

Figure 1:
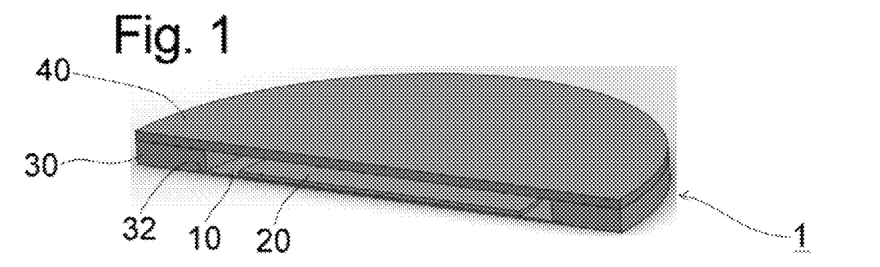
FIG. 1 is a perspective sectional view of a fluid pressure detection device 1 according to a first reference example of the present invention.

With reference to FIG. 1 to FIG. 21, a fluid pressure detection device 1 according to a first reference example of the present invention will be described hereinunder. The fluid pressure detection device 1 is used in oil pressure gauges, water gauges and blood pressure gauges. As shown in FIG. 1, the fluid pressure detection device 1 comprises a substrate 10 (diaphragm), a piezoelectric element 20, a support body 30 and a lid body 40. The substrate 10 is, for example, a plate-like or sheet-like substrate having a thickness of 10 to 200 μm and made of a metal such as stainless steel. The top surface (one surface) of the substrate 10 is a surface for mounting the piezoelectric element 20. The bottom surface (the other surface) of the substrate 10 is a surface to be pressed against a tube 7 shown in FIG. 9. The piezoelectric element 20 is, for example, a piezoelectric ceramic having a thickness of 10 to 200 μm and formed (mounted) on the top surface (the one surface) of the substrate 10. A metal electrode (for example a gold electrode having a thickness of several μm to 20 μm formed by gold sputtering) for taking out signals is formed on both surfaces of the piezoelectric element 20 but not shown in FIG. 1. The metal electrodes and the piezoelectric element 20 constitute a piezoelectric unimorph. The substrate 10 and the piezoelectric element 20 are substantially circular in the example of FIG. 1.

Figure 2:
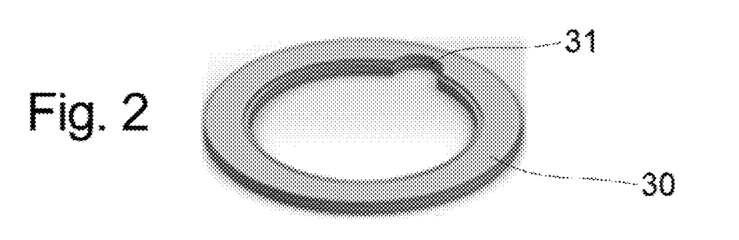
FIG. 2 is a perspective view of a support body 30 in FIG. 1.
Figure 3:
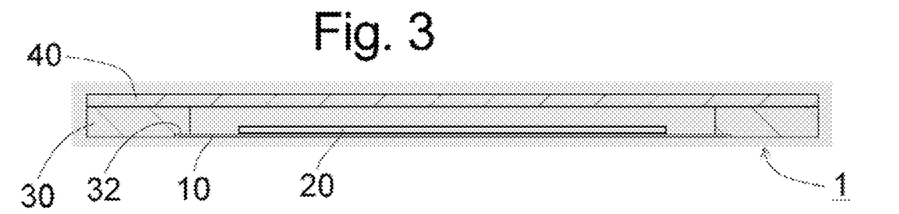
FIG. 3 is a sectional view of the fluid pressure detection device 1.

The support body 30 is a circularly annular member having a much larger thickness (height) than the piezoelectric element 20 and made of a rigid material such as stainless steel. The support body 30 is provided to surround the piezoelectric element 20. As shown in FIG. 1 and FIG. 3, the support body 30 has a stepped part 32 in the vicinity of the inner edge part of the bottom surface. With the stepped part 32, the support body 30 supports the top surface of the substrate 10 in the vicinity of the outer edge. As shown in FIG. 2, the support body 30 has a notch 31 at the inner edge for leading out wires.

Figure 7:
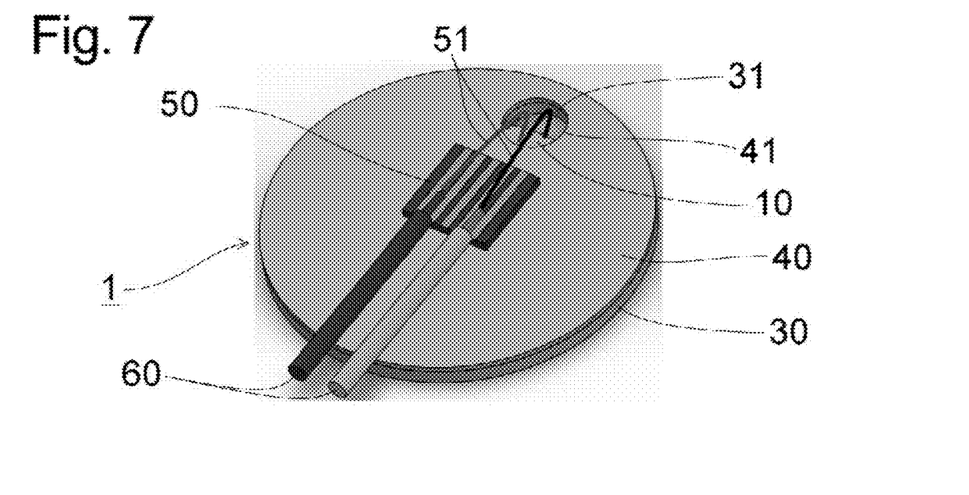
FIG. 7 is a perspective view of the fluid pressure detection device 1 including the constitution of signal extraction.
Figure 8:
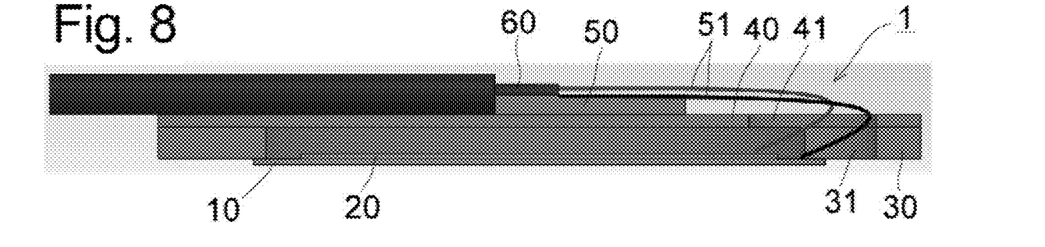
FIG. 8 is a sectional view of the fluid pressure detection device 1 including the constitution of signal extraction.

The lid body 40 is a plate-like or sheet-like body having substantially the same shape as the substrate 10 in plane view and made of a metal such as stainless steel. The lid body 40 is mounted to the upper end (one end) of the support body 30 to close the top opening (one-end opening) of the support body 30. As shown in FIG. 7, the lid body 40 has a through hole 41 for leading out wires. The through hole 41 communicates with the notch 31 of the support body 30. On the top surface of the lid body 40, a terminal part 50 is provided. The terminal part 50 is electrically connected to the piezoelectric element 20 by wires 51. From the terminal part 50, cables 60 extend for connecting to a circuit (FIG. 11 or FIG. 13) in an unshown measuring instrument.

Figure 4:
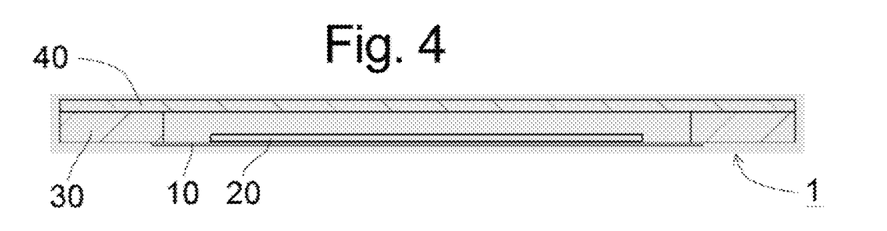
FIG. 4 is a sectional view showing another constitution example of the fluid pressure detection device 1.
Figure 5:
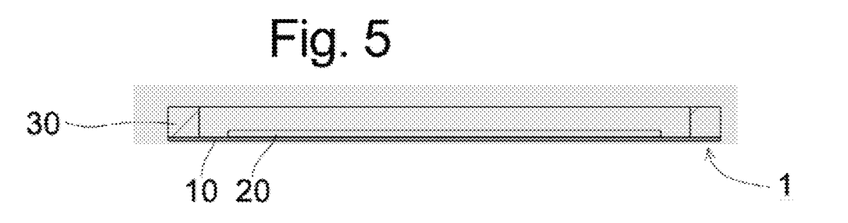
FIG. 5 is a sectional view showing still another constitution example of the fluid pressure detection device 1.
Figure 6:
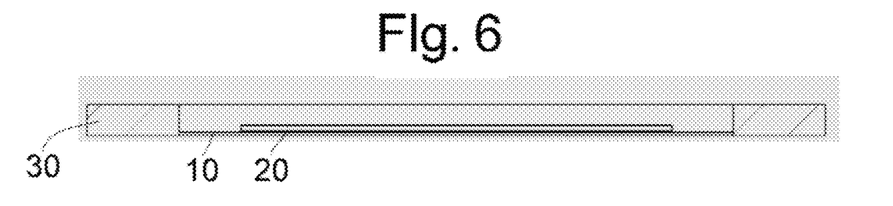
FIG. 6 is a sectional view showing still another constitution example of the fluid pressure detection device 1.

The support of the substrate 10 with the support body 30 is not limited to support with the stepped part 32 shown in FIG. 1 and FIG. 3. The substrate 10 may be supported by the bottom surface of the support body 30 having no stepped part 32 as shown in FIG. 4. Further, as shown in FIG. 5, the lid body 40 may not be provided. In a constitution example shown in FIG. 6, the outer edge (outer peripheral surface) of the substrate 10 is supported by the inner peripheral surface of the support body 30. But the support structures shown in FIGS. 3 to 5 are preferred from the viewpoint of the reproducibility of pressure detection.

Figure 9:
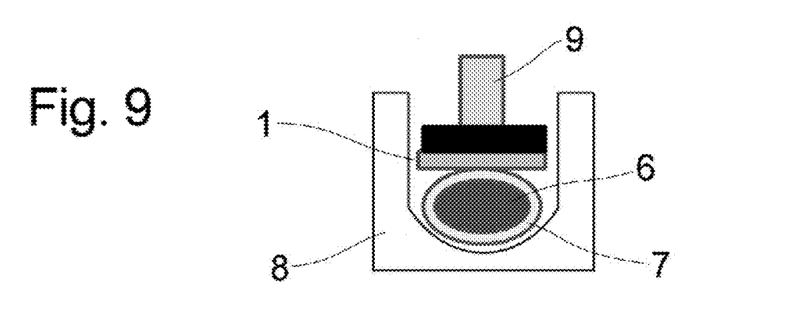
FIG. 9 is a schematic diagram showing that the fluid pressure detection device 1 is directly pressed against a tube 7.

FIG. 9 is a schematic diagram showing that the fluid pressure detection device 1 is directly pressed against the tube 7. This schematic diagram shows the cross section of an evaluation device for quantitatively evaluating the fluid pressure detection device 1. The tube 7 is, for example, a silicone tube having flexibility or viscoelasticity. The tube 7 is held in a tube holder 8 having a U-shaped cross section. The outer diameter of the tube 7 is 6 mm. A fluid 6 supplied from an unshown piston pump flows (transferred with pulsation) inside the tube 7. When detecting the pressure of the fluid 6, by a force gauge 9 the fluid pressure detection device 1 is pressed from the lid body 40 side (the support body 30 is pressed from a side opposite to the substrate 10) so that the other surface of the substrate 10 is pressed against the tube 7 to deform the tube 7. Measurement results which will be given hereinafter were obtained when the fluid 6 was supplied at 96 bpm by the pumping function of the above piston pump. The pressure of the fluid 6 was also directly detected by an unshown pressure sensor (Model AP-13S of KEYENCE CORPORATION) to evaluate the output of the fluid pressure detection device 1.

Figure 10:
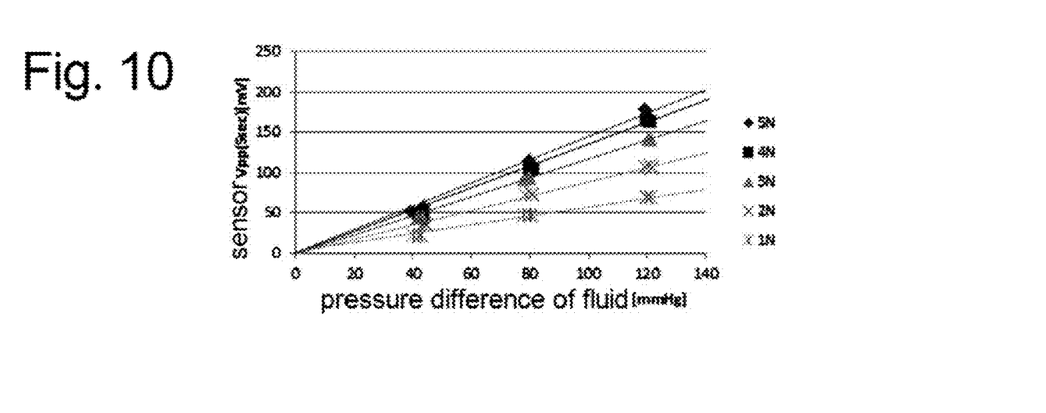
FIG. 10 is a graph showing the relationship between the pressure difference of a fluid 6 flowing inside the tube 7 and a sensor output when the pressing force applied to the fluid pressure detection device 1 against the tube 7 is set to 1N, 2N, 3N, 4N and 5N.

FIG. 10 is a graph showing the relationship between the pressure difference of the fluid 6 flowing inside the tube 7 and the output of the sensor when the pressing force applied to the fluid pressure detection device 1 against the tube 7 was set to 1N, 2N, 3N, 4N and 5N. This graph is a linear approximation graph of the peak-peak value of the output voltage (output voltage Vout1 of a circuit shown in FIG. 11 which will be described hereinafter) of the fluid pressure detection device 1 for each pressing force when measurement was made by setting the pressure difference to 40 mmHg (minimum pressure of 50 mmHg to maximum pressure of 90 mmHg), 80 mmHg (minimum pressure of 50 mmHg to maximum pressure of 130 mmHg) and 120 mmHg (minimum pressure of 50 mmHg to maximum pressure of 170 mmHg). It could be confirmed from FIG. 10 that the pressure difference of the fluid 6 flowing inside the tube 7 and the output voltage of the fluid pressure detection device 1 have high correlation with a correlation coefficient of more than 0.98 at any pressing force, and are substantially in proportion to each other. The pressing force was set to 3N in the following measurement.

Figure 11:
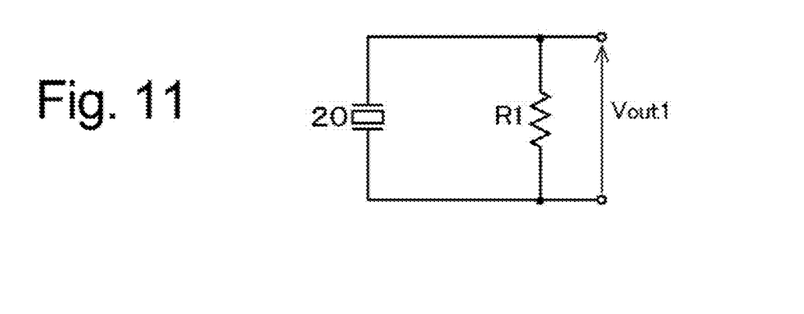
FIG. 11 is a circuit diagram showing an example of an I-V conversion circuit (impedance conversion circuit) which converts the output current of the piezoelectric element 20 of the fluid pressure detection device 1 into voltage.
Figure 12:
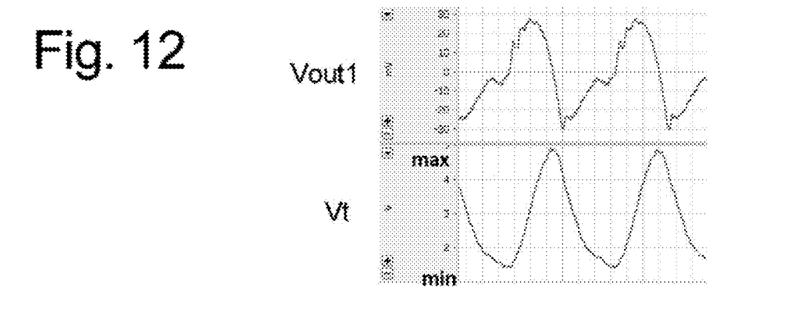
FIG. 12 is a diagram showing the waveform of the output voltage Vout1 of the circuit shown in FIG. 11 and the waveform of a direct detection value Vt obtained by directly detecting the pressure of the fluid 6 with an unshown water pressure sensor.

FIG. 11 is a circuit diagram showing an example of an I-V conversion circuit (impedance conversion circuit) which converts the output current of the piezoelectric element 20 of the fluid pressure detection device 1 into voltage. This circuit constitutes a closed loop with the piezoelectric element 20 and a resistor R1, and an output voltage Vout1 appears at both ends of the resistor R1. The output voltage Vout1 is in proportion to the time differential of a charge generated in the piezoelectric element 20, that is, the pressure change rate of the fluid 6, where the proportional constant is the resistance value of the resistor R1. FIG. 12 is a waveform diagram showing the waveform of the output voltage Vout1 of the circuit shown in FIG. 11 and the waveform of a direct detection value Vt obtained by directly detecting the pressure of the fluid 6 with an unshown water pressure sensor. It could be confirmed from FIG. 12 that the output voltage Vout1 is linked with the inclination of the direct detection value Vt. The difference in the fluid pressure (maximum pressure–minimum pressure) produced by the beating of a piston pump can be detected by the circuit shown in FIG. 11.

Figure 13:
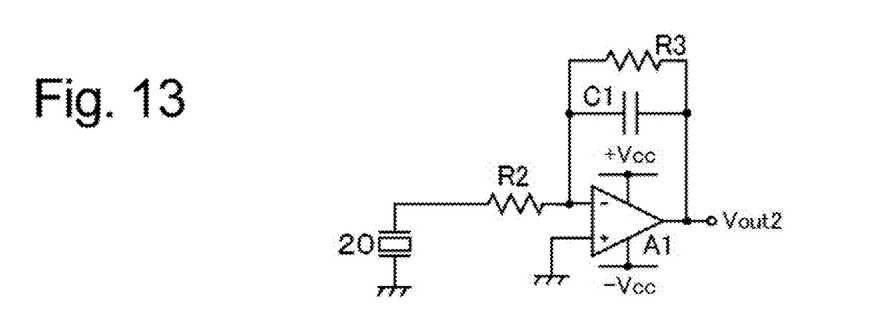
FIG. 13 is a circuit diagram showing an example of an integrating circuit which integrates the output current of the piezoelectric element 20 of the fluid pressure detection device 1.

FIG. 13 is a circuit diagram showing an example of an integrating circuit which integrates the output current of the piezoelectric element 20 of the fluid pressure detection device 1. This circuit is an integrating circuit utilizing an operation amplifier A1 and accumulates the output current of the piezoelectric element 20 in a capacitor C1 provided between the output terminal and the inverted input terminal of the operation amplifier A1. One end of the piezoelectric element 20 is connected to the ground as a fixed voltage terminal. The other end of the piezoelectric element 20 is connected to one end of a resistor R2. The other end of the resistor R2 is connected to the inverted input terminal of the operation amplifier A1. The non-inverted input terminal of the operation amplifier A1 is connected to the ground. The capacitor C1 and a resistor R3 are connected in parallel to each other between the output terminal and the inverted input terminal of the operation amplifier A1. The resistor R3 is provided to prevent the saturation of the output of the operation amplifier A1. The operation amplifier A1 is driven by two power sources and connected to a positive side power line (voltage Vcc) and to a negative side power line (voltage –Vcc). Since the inverted input terminal voltage of the operation amplifier A1 becomes substantially equal to ground potential by a virtual short, an output voltage Vout2 which appears at the output terminal of the operation amplifier A1 is voltage between both ends of the capacitor C1. The output voltage Vout2 is in proportion to the integral of the output current of the piezoelectric element 20 where the proportional constant is the reciprocal of the capacitance value of the capacitor C1. The original charge generation output waveform of the piezoelectric element 20 is obtained by the circuit shown in FIG. 13, thereby making it possible to calculate a pressure change.

Figure 14:
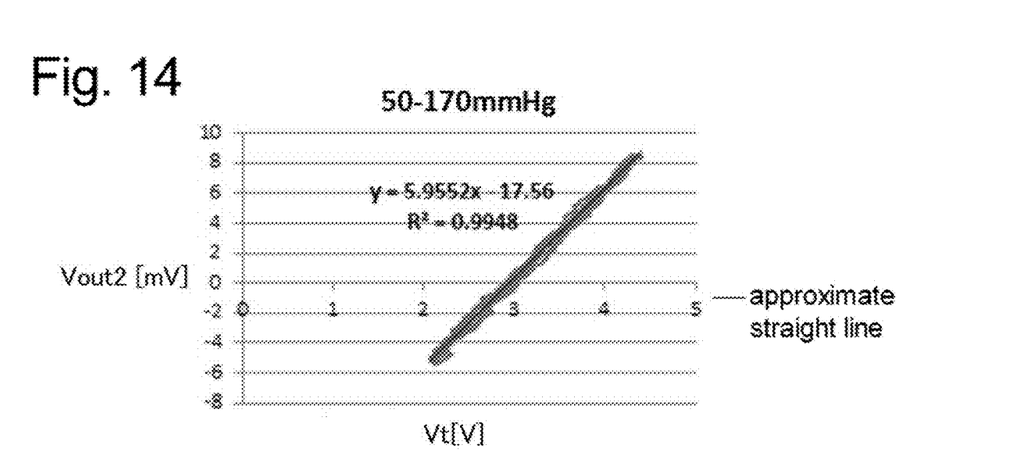
FIG. 14 is a diagram showing correlation between the output voltage Vout2 of the circuit shown in FIG. 13 and the direct detection value Vt obtained by directly detecting the pressure of the fluid 6 with an unshown water pressure sensor when the fluid 6 flowing inside the tube 7 is pulsated with a minimum pressure of 50 mmHg to a maximum pressure of 170 mmHg.

FIG. 14 is a diagram showing correlation between the output voltage Vout2 of the circuit shown in FIG. 13 and the direct detection value Vt obtained by directly detecting the pressure of the fluid 6 with an unshown water pressure sensor when the fluid 6 flowing inside the tube 7 is pulsated with a minimum pressure of 50 mmHg to a maximum pressure of 170 mmHg. Results shown in FIG. 14 were obtained by measuring for 10 seconds at a sampling frequency of 1 kHz and the number of data pieces was 10,000. These conditions are the same as in the correlation graphs shown in FIG. 15, FIG. 19 and FIG. 20. It could be confirmed from FIG. 14 that the output voltage Vout2 and the direct detection value Vt have high correlation with a correlation coefficient of more than 0.99. Therefore, the difference between the minimum pressure and the maximum pressure of the fluid 6 flowing inside the tube 7 can be detected from the peak-peak value of the output voltage Vout2.

Figure 15:
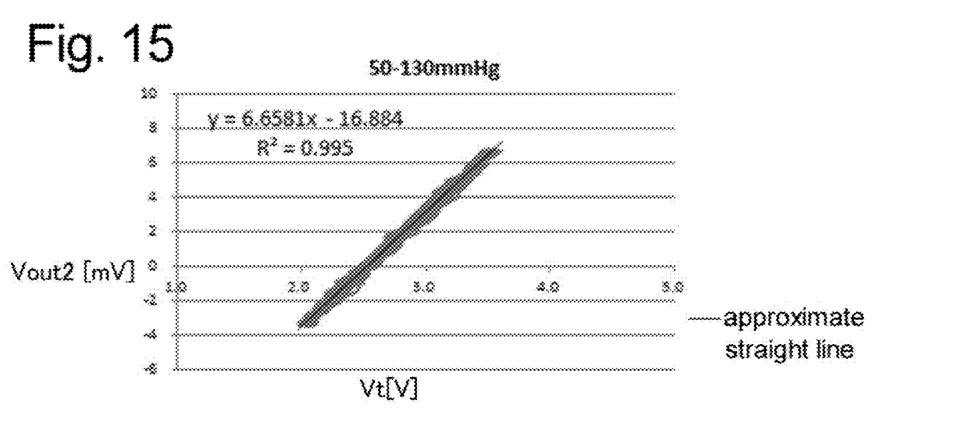
FIG. 15 is a diagram showing correlation between the output voltage Vout2 of the circuit shown in FIG. 13 and the direct detection value Vt obtained by directly detecting the pressure of the fluid 6 with an unshown water pressure sensor when the fluid 6 flowing inside the tube 7 is pulsated with a minimum pressure of 50 mmHg to a maximum pressure of 130 mmHg.
Figure 16:
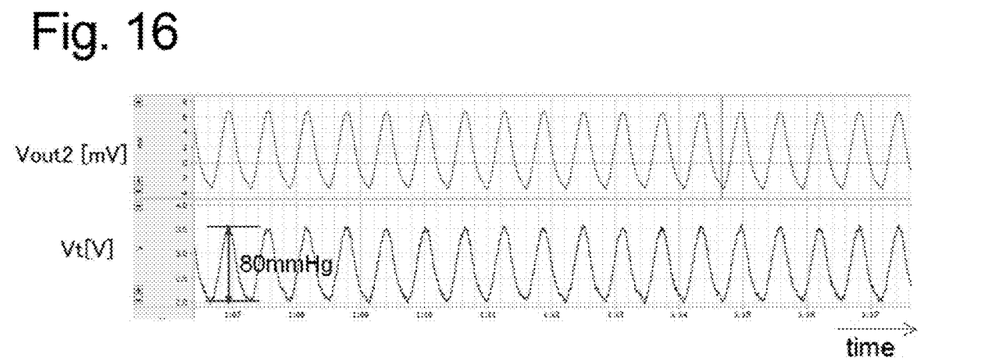
FIG. 16 is a diagram showing the waveform of the output voltage Vout2 of the circuit shown in FIG. 13 and the waveform of the direct detection value Vt obtained by directly detecting the pressure of the fluid 6 with an unshown water pressure sensor when the fluid 6 flowing inside the tube 7 is pulsated with a minimum pressure of 50 mmHg to a maximum pressure of 130 mmHg.

FIG. 15 is a diagram showing correlation between the output voltage Vout2 of the circuit shown in FIG. 13 and the direct detection value Vt obtained by directly detecting the pressure of the fluid 6 with an unshown water pressure sensor in cases where the fluid 6 flowing inside the tube 7 is pulsated with a minimum pressure of 50 mmHg to a maximum pressure of 130 mmHg. FIG. 16 is a diagram showing the waveform of the output voltage Vout2 of the circuit shown in FIG. 13 and the waveform of the direct detection value Vt obtained by directly detecting the pressure of the fluid 6 with an unshown water pressure sensor in the above case. It could be confirmed from FIG. 15 that the output voltage Vout2 and the direct detection value Vt have high correlation as in FIG. 14. Also, it could be confirmed from FIG. 16 that the waveform of the output voltage Vout2 and the waveform of the direct detection value Vt are almost the same.

Figure 17:
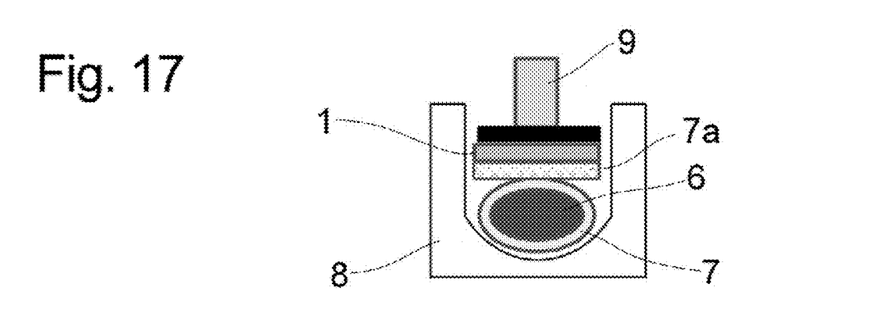

FIG. 17 is a schematic diagram showing that the fluid pressure detection device 1 is pressed against the tube 7 through human skin gel 7a. This schematic diagram shows the cross section of an evaluation device for quantitatively evaluates the fluid pressure detection device 1. FIG. 17 differs from FIG. 9 in that the human skin gel 7a having flexibility or viscoelasticity is added, but is the same in other points. By adding the human skin gel 7a, a state is made close to the pressure measurement (blood pressure measurement) of a blood flowing inside a blood vessel of a human body.

Figure 18:
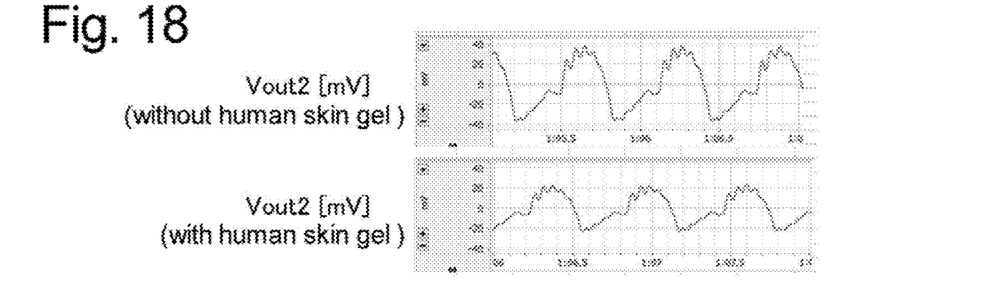
FIG. 18 is a waveform diagram of the output voltage Vout2 of the circuit shown in FIG. 13 when the fluid 6 flowing inside the tube 7 is pulsated with a minimum pressure of 50 mmHg to a maximum pressure of 150 mmHg in a case where the fluid pressure detection device 1 is pressed against the tube 7 without the human skin gel 7a (FIG. 9) and in a case where the fluid pressure detection device 1 is pressed against the tube 7 through the human skill gel 7a (FIG. 17).

FIG. 18 is a waveform diagram of the output voltage Vout2 of the circuit shown in FIG. 13 when the fluid 6 flowing inside the tube 7 is pulsated with a minimum pressure of 50 mmHg to a maximum pressure of 150 mmHg in a case where the fluid pressure detection device 1 is pressed against the tube 7 without the human skin gel 7a (FIG. 9) and in a case where the fluid pressure detection device 1 is pressed against the tube 7 through the human skin gel 7a (FIG. 17). It could be confirmed from FIG. 18 that though sensitivity (amplitude) drops, almost the same waveform is obtained between when the fluid pressure detection device 1 is pressed through the human skin gel 7a against the tube 7 and when it is pressed not through the human skin gel 7a against the tube 7.

Figure 19:
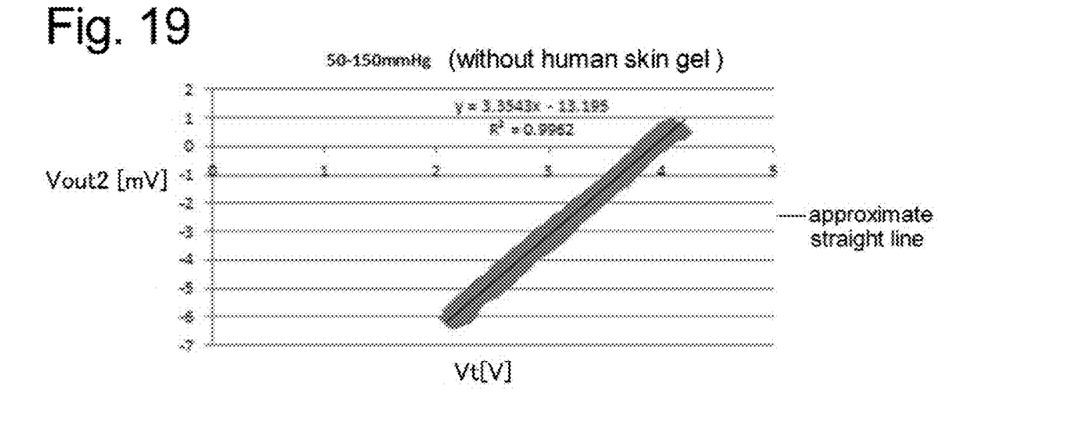
FIG. 19 is a diagram showing correlation between the output voltage Vout2 of the circuit shown in FIG. 13 and the direct detection value Vt obtained by directly detecting the pressure of the fluid 6 with an unshown water pressure sensor when the fluid pressure detection device 1 is pressed against the tube 7 without the human skin gel 7a in a case where the fluid 6 flowing inside the tube 7 is pulsated with a minimum pressure of 50 mmHg to a maximum pressure of 150 mmHg.
Figure 20:
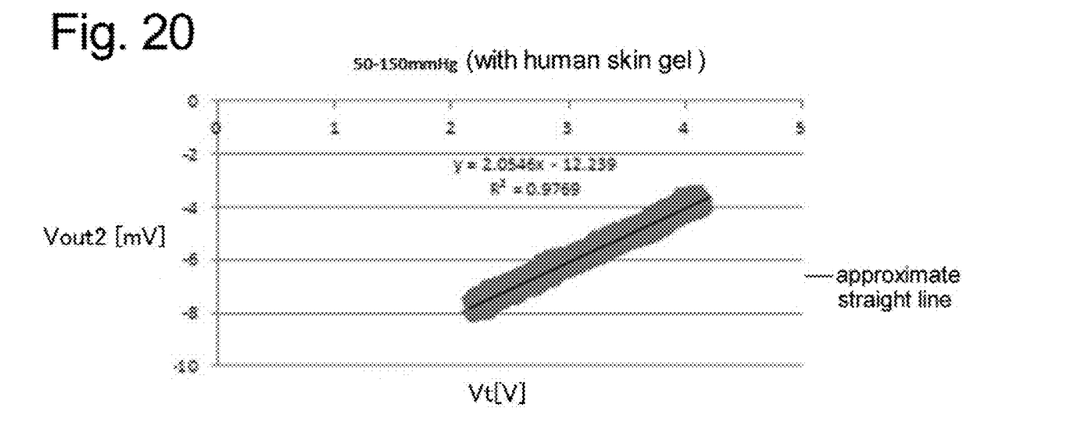
FIG. 20 is a diagram showing correlation between the output voltage Vout2 of the circuit shown in FIG. 13 and the direct detection value Vt obtained by directly detecting the pressure of the fluid 6 with an unshown water pressure sensor when the fluid pressure detection device 1 is pressed against the tube 7 through the human skin gel 7a in the above case.

FIG. 19 is a diagram showing correlation between the output voltage Vout2 of the circuit shown in FIG. 13 and the direct detection value Vt obtained by directly detecting the pressure of the fluid 6 with an unshown water pressure sensor when the fluid pressure detection device 1 is pressed against the tube 7 without the human skin gel 7a in a case where the fluid 6 flowing inside the tube 7 is pulsated with a minimum pressure of 50 mmHg to a maximum pressure of 150 mmHg. FIG. 20 is a diagram showing correlation between the output voltage Vout2 of the circuit shown in FIG. 13 and the direct detection value Vt obtained by directly detecting the pressure of the fluid 6 with an unshown water pressure sensor when the fluid pressure detection device 1 is pressed against the tube 7 through the human skin gel 7a in the above case. In the measurement which is the basis of the results of FIG. 20, the human skin gel (Model H0-2) of EXSEAL CORPORATION was used as the human skin gel 7a. It could be confirmed from comparison between FIG. 19 and FIG. 20 that when the fluid pressure detection device 1 is pressed against the tube 7 through the human skin gel 7a, the output voltage Vout2 and the direct detection value Vt have high correlation with a correlation coefficient of more than 0.97, though the correlation coefficient slightly drops compared with the case where the fluid pressure detection device 1 is pressed against the tube 7 without the human skin gel 7a.

Figure 21:
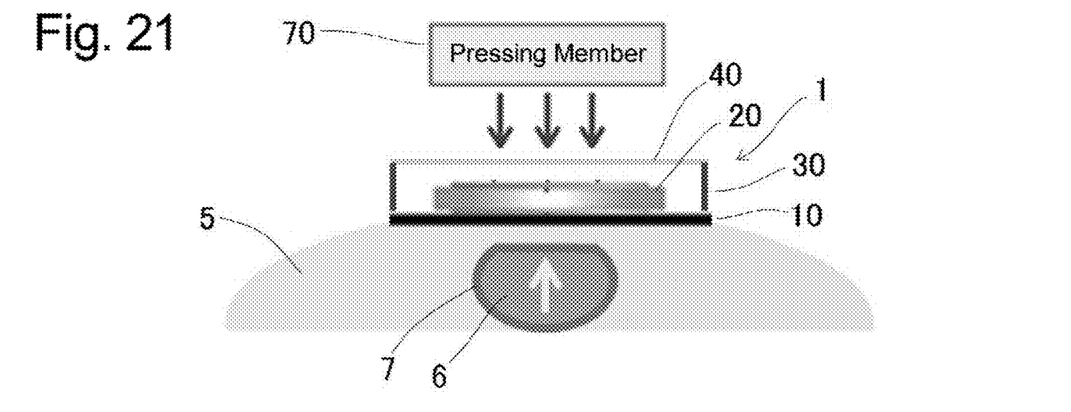
FIG. 21 is a schematic diagram showing that the fluid pressure detection device 1 is pressed against the surface (skin) of a human body 5 to deform the tube 7 which is an artery in the human body 5.

FIG. 21 is a schematic diagram showing that the fluid pressure detection device 1 is pressed against the surface (skin) of a human body 5 to deform the tube 7 which is an artery in the human body 5. A pressing member 70 is used to press the bottom surface of the substrate 10 against the tube 7 by pressing the support body 30 from a side opposite to the substrate 10. The pressing member 70 may be just a belt or an adhesive tape such as an adhesive bandage having a viscous surface. By pressing the bottom surface of the substrate 10 against the tube 7 through the support body 30 to deform the tube 7 as shown in FIG. 21, the difference between the minimum pressure (minimum blood pressure) and the maximum pressure (maximum blood pressure) of the fluid 6 (blood) flowing inside the tube 7 can be detected from outside the human body 5 more accurately than before. The existence of the support body 30 makes it possible to carry out stable detection with excellent reproducibility.

First Measurement

Figure 22A:
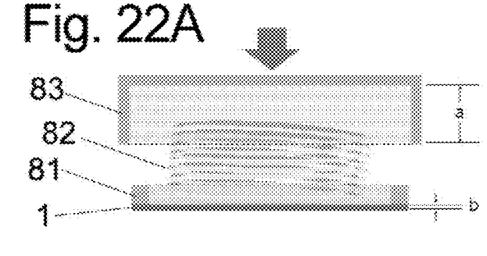
FIG. 22A is a schematic sectional view before measurement and FIG. 22B is a schematic sectional view during measurement.
Figure 22B:
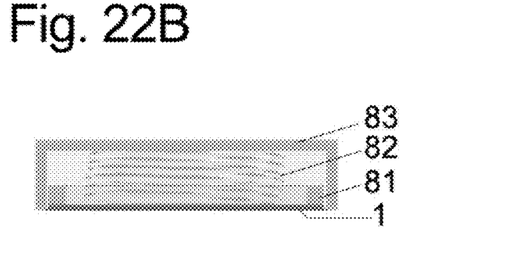

FIG. 22A and FIG. 22B are schematic sectional views of a measuring instrument used in first to third measurements. FIG. 22A is of before measurement. FIG. 22B is of during measurement. This measuring instrument was made by combining a frame body 81, a round wire coil spring 82 and a cap 83 with the fluid pressure detection device 1 of FIG. 7 whose support body 30 having an outer diameter of 12 mm. The frame body 81 is provided to guide the pressing of the cap 83 and hold the pressed cap 83. The round wire coil spring 82 has an outer diameter of 8 mm, a total length of 15 mm and a spring constant of 0.1 N/mm. The cap 83 is made of polyurethane and has an outer diameter of 18 mm and an inner diameter of 14 mm. The spot facing depth "a" of the cap 83, the thickness "b" of the fluid pressure detection device 1 and the total length (natural length) of the round wire coil spring 82 were set to ensure that a pressure of 40 mmHg should be applied to the top surface of the fluid pressure detection device 1 by the round wire coil spring 82 when the cap 83 was pressed to the lower limit position as shown in FIG. 22B.

The above measuring instrument was fixed to the skin (position at which a pulse can be felt) above the superficial temporal artery of each of eight subjects by using the surgical tape of 3M Company while the round wire coil spring 82 was compressed as shown in FIG. 22B, and the output voltage Vout1 of the I-V conversion circuit (impedance conversion circuit) of FIG. 11 was measured. As a result, stable output was obtained in all the subjects. Therefore, it was found that, when a pressure of 40 mmHg is applied to the top surface of the fluid pressure detection device 1, normal blood pressure measurement is possible above the superficial temporal artery.

Second Measurement

The same measurement as in the first measurement was made on the common carotid artery of each of eight subjects. That is, the above measuring instrument was fixed to the skin (position at which a pulse can be felt) above the common carotid artery in the same manner as in the first measurement to measure the output voltage Vout1. As a result, stable output was obtained in all the subjects. Therefore, it was found that when a pressure of 40 mmHg is applied to the top surface of the fluid pressure detection device 1, normal blood pressure measurement is possible above the common carotid artery.

Third Measurement

The same measurement as in the first measurement was made on the radial artery of each of eight subjects. That is, the above measuring instrument was fixed to the skin (position at which a pulse can be felt) above the radial artery in the same manner as in the first measurement to measure the output voltage Vout1. In this measurement, three types of round wire coil springs 82 were used. That is, in addition to a type used in Example 1, a round wire coil spring 82 having an outer diameter of 8 mm, a total length of 20 mm and a spring constant of 0.1 N/mm, and a round wire coil spring 82 having an outer diameter of 10 mm, a total length of 15 mm and a spring constant of 0.2 N/mm were used. And then by adjusting the spot facing depth of the cap 83, a pressure of 40 mmHg, 60 mmHg, 80 mmHg, 100 mmHg or 120 mmHg was applied to the top surface of the fluid pressure detection device 1 to carry out the above measurement.

Figure 23:
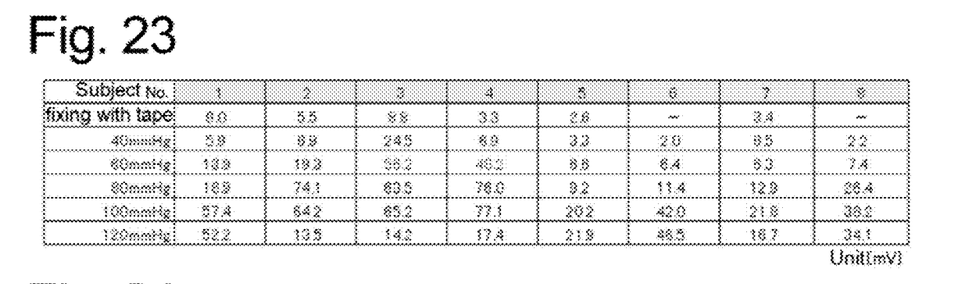
FIG. 23 is a table showing measurement results (peak-peak values Vpp of output voltages Vout1) in the third measurement.
Figure 24:
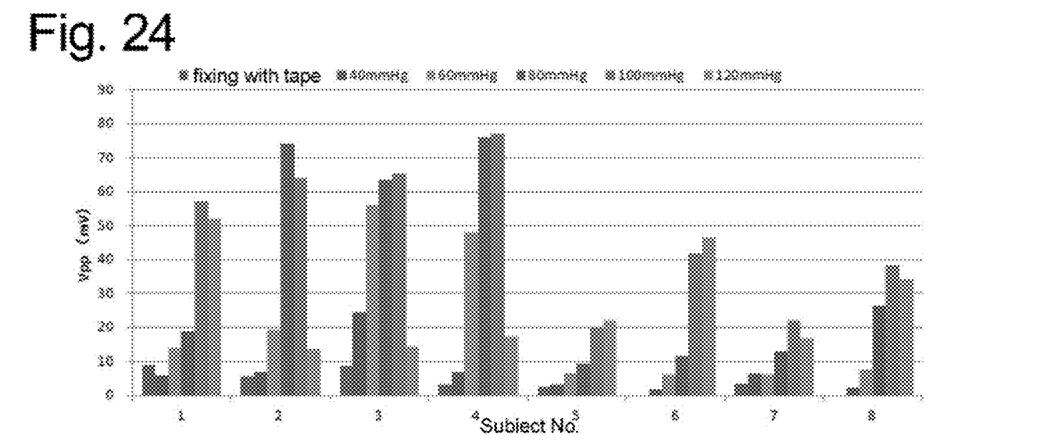
FIG. 24 is a bar graph obtained from the table of FIG. 23.

FIG. 23 is a table showing measurement results (peak-peak values Vpp of output voltages Vout1) in the third measurement. FIG. 24 is a bar graph obtained from the table of FIG. 23. The numerical values of the measurement results are average values of the peak-peak values Vpp (maximum−minimum) of last 10 beats in a measurement time of 30 seconds. In FIG. 23 and FIG. 24, the expression "fixing with tape" means that the fluid pressure detection device 1 is fixed with a surgical tape without using the frame body 81, the round wire coil spring 82 and the cap 83 to prevent its displacement, without being conscious of pressure. In the case of "fixing with a tape", output could not be obtained in two subjects No. 6 and No. 8 as shown in FIG. 23 and FIG. 24. Meanwhile, when a pressure of 40 mmHg, 60 mmHg, 80 mmHg, 100 mmHg or 120 mmHg was applied to the top surface of the fluid pressure detection device 1, output could be obtained in all the subjects. Therefore, it was found that when a pressure of 40 mmHg is applied to the top surface of the fluid pressure detection device 1, normal blood pressure measurement is possible above the radial artery.

Although a pressure at which the highest peak-peak value Vpp was obtained differed according to each subject, in all the subjects, a higher peak-peak value Vpp was obtained when a 60 mmHg pressure was applied than when a 40 mmHg pressure was applied, and a higher peak-peak value Vpp was obtained when a 80 mmHg pressure was applied than when a 60 mmHg pressure was applied. Further, in all the subjects except subject No. 2, a higher peak-peak value Vpp was obtained when a 100 mmHg pressure was applied than when a 80 mmHg pressure was applied. Meanwhile, in all the subjects except subjects No. 5 and No. 6, a lower peak-peak value Vpp was obtained when a 120 mmHg pressure was applied than when a 100 mmHg pressure was applied. From the viewpoint of a burden on each subject, a lower pressure is more preferred. Therefore, in consideration of balance between sensitivity and a burden on subject, it was found that a pressure of not more than 100 mmHg or not more than 80 mmHg is preferred.

For the measurement of blood pressure with the fluid pressure detection device 1, it is not necessary to use the frame body 81, the round wire coil spring 82 and the cap 83 as in the above measurement instrument. To obtain a required pressure, an elastic body such as rubber may be placed on the fluid pressure detection device 1, and the fluid pressure detection device 1 may be fixed on a measurement point with a surgical tape from above the elastic body. Alternatively, the fluid pressure detection device 1 may be fixed on a measurement point with an elastic tape stretched by a predetermined length. At this point, a spacer (such as a pad) may be placed on the fluid pressure detection device 1 to obtain a required thickness. The fluid pressure detection device 1 and members for fixing it on the measurement point may be as a whole considered as a fluid pressure detection device.

Figure 25:
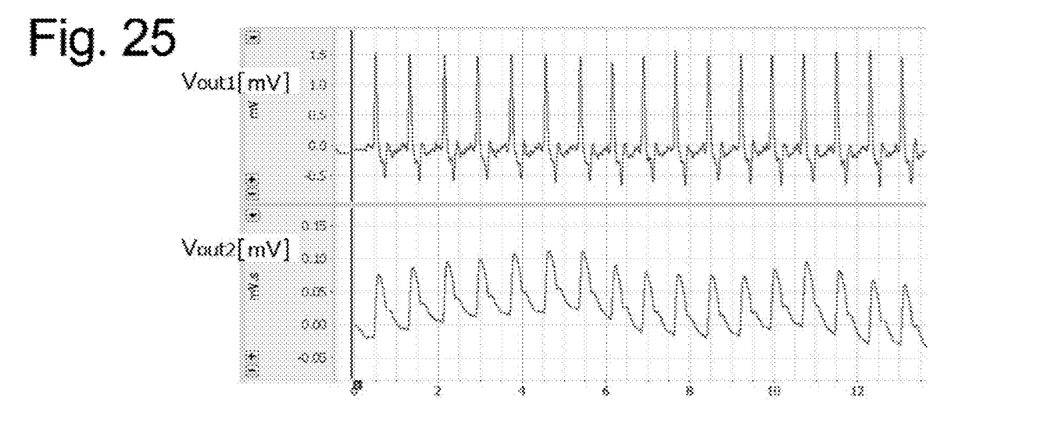
FIG. 25 is a diagram showing the waveform of the output voltage Vout1 of the I-V conversion circuit (impedance conversion circuit) of FIG. 11 and the waveform of the output voltage Vout2 of the integrating circuit of FIG. 13 all of which were obtained from measurement (40 mmHg) on a subject No. 8 in the third measurement.

FIG. 25 is a diagram showing the waveform of the output voltage Vout1 of the I-V conversion circuit (impedance conversion circuit) of FIG. 11 and the waveform of the output voltage Vout2 of the integrating circuit of FIG. 13 both of which were obtained from measurement (40 mmHg)

on a subject No. 8 in the third measurement. It could be confirmed from FIG. 25 that waveforms having little noise were obtained.

Second Reference Example

Figure 26A:
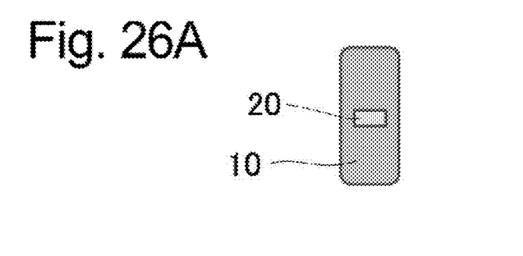
FIG. 26A is a plane view of a first constitution example and FIG. 26B is a plane view of a second constitution example.
Figure 26B:
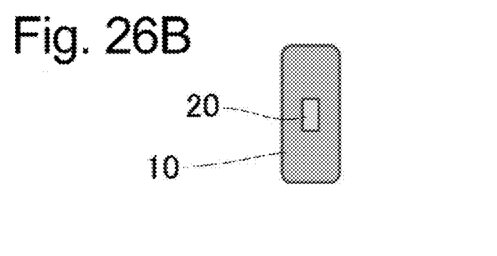
Figure 27A:
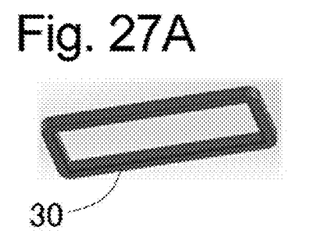
FIG. 27A is a perspective view of an all-side support type.
Figure 27B:
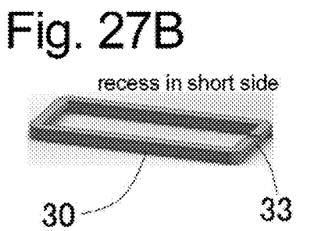
FIG. 27B is a perspective view of a long-side support type (recess in a short side) and FIG. 27C is a perspective view of a short-side support type (recess in a long side).
Figure 27C:
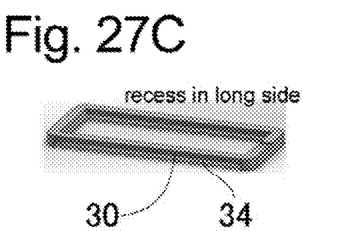

FIG. 26A and FIG. 26B are plane views of the substrate 10 and the piezoelectric element 20 of a fluid pressure detection device according to a second reference example of the present invention. FIG. 26A shows a first constitution example and FIG. 26B shows a second constitution example. The fluid pressure detection device of this reference example differs from the fluid pressure detection device of the first reference example in that the substrate 10 and the piezoelectric element 20 are substantially rectangular and the support body 30 is rectangularly annular like the outer shape of the substrate 10, but is the same in other points. For the detection of the pressure of the fluid 6, the longitudinal direction of the substrate 10 and the extending direction of the tube 7 are made parallel to each other. In the first constitution example shown in FIG. 26A, the long sides of the piezoelectric element 20 are substantially vertical to the long sides of the substrate 10 (substantially parallel to the short sides). In the second constitution example shown in FIG. 26B, the long sides of the piezoelectric element 20 are substantially parallel to the long sides of the substrate 10. When the support body 30 is of an all-side support type shown in FIG. 27A, it supports all the sides (four sides) and therearound of the substrate 10. When the support body 30 is of a long-side support type (having a recessed part 33 in a lower part of a short side) shown in FIG. 27B, it supports two long sides and therearound of the substrate 10 (no contact with a short side). When the support body 30 is of a short-side support type (having a recessed part 34 in a lower part of a long side) shown in FIG. 27C, it supports two short sides and therearound of the substrate 10 (no contact with a long side). In the following description, the support body 30 is of the all-side support type shown in FIG. 27A.

Figure 28:
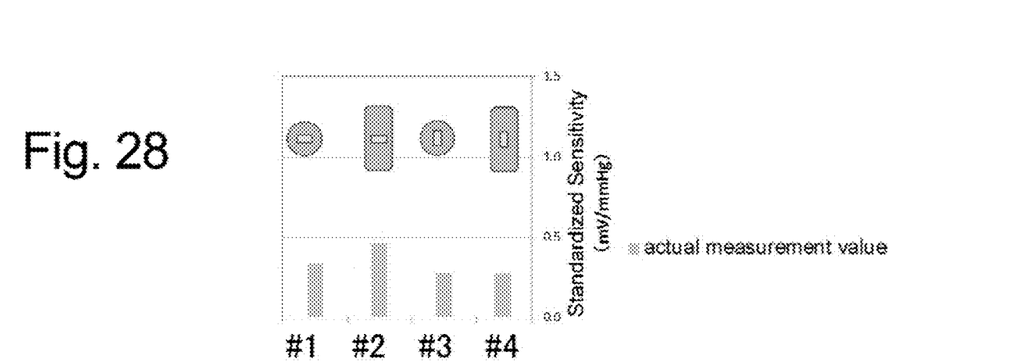
FIG. 28 is a bar graph showing comparison between the standardized sensitivity (mV/mmHg) of each of the fluid pressure detection devices of the second reference example and the standardized sensitivity of each of the fluid pressure detection devices of comparative examples.

FIG. 28 is a bar graph showing comparison between the standardized sensitivity (mV/mmHg) of each of the fluid pressure detection devices of the second reference example and the standardized sensitivity of each of the fluid pressure detection devices of comparative examples. The term "standardized sensitivity" is obtained by dividing the peak-peak value of the output voltage Vout1 of the circuit shown in FIG. 11 by a difference between the minimum pressure and the maximum pressure and based on an actual measurement value. In FIG. 28, #1 represents a comparative example in which the substrate 10 is circular with a diameter of 9 mm, the support body 30 is circularly annular and the piezoelectric element 20 has the same shape as that of the first constitution example of this reference example. #2 represents the first constitution example of this reference example in which the size of substrate 10 is 8 mm×18 mm. #3 represents a comparative example in which the substrate 10 is circular with a diameter of 9 mm, the support body 30 is circularly annular and the piezoelectric element 20 has the same shape as that of the second constitution example of this reference example. #4 represents the second constitution example of this reference example in which the size of the substrate 10 is 8 mm×18 mm. In all of #1 to #4, the size of the piezoelectric element is 2 mm×4 mm.

It was found from comparison between #1 and #2 that higher sensitivity is obtained with the rectangular substrate 10 than with the circular substrate 10 when the longitudinal direction of the piezoelectric element 20 is parallel to the short-length direction of the substrate 10 even if the short sides of the rectangle are shorter than the diameter of the circle. It was also found from comparison between #3 and #4 that there is not so much difference in sensitivity between the circular substrate 10 and the rectangular substrate 10 when the longitudinal direction of the piezoelectric element 20 is parallel to the longitudinal direction of the substrate 10.

Figure 29:
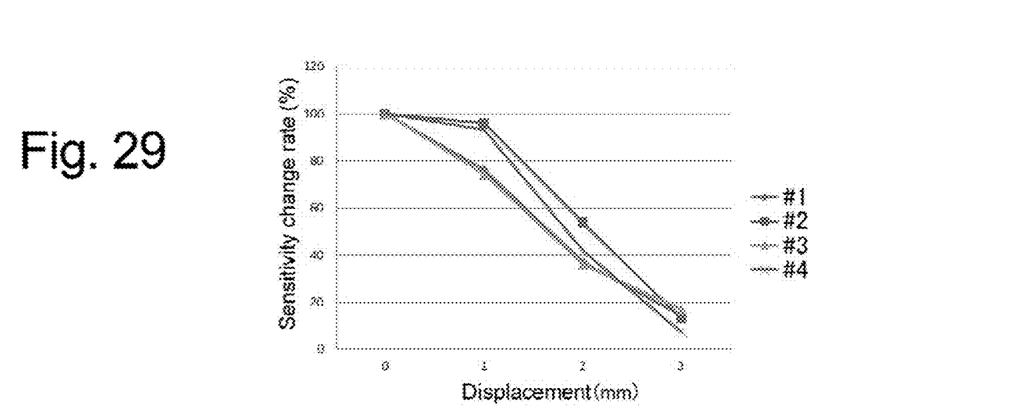
FIG. 29 is a graph showing the relationship between the displacement against the tube 7 and sensitivity change rate in the fluid pressure detection devices of the second reference example and the fluid pressure detection devices of the comparative examples.

FIG. 29 is a graph showing the relationship between the displacement against the tube 7 and sensitivity change rate in the fluid pressure detection devices of the second reference example and the fluid pressure detection devices of the comparative examples. The displacement on the abscissa axis in FIG. 29 is the relative amount of displacement of the tube 7 in the short-length direction of the substrate 10 while the extending direction of the tube 7 remains parallel to the longitudinal direction of the substrate 10. "0 mm" on the abscissa axis means that the tube 7 passes the center of the substrate 10 in the short-length direction. It was found from FIG. 29 that when the amount of displacement is not more than 2 mm, the reduction of sensitivity caused by displacement is suppressed more in #2 and #4 in which the substrate 10 is rectangular than #1 and #3 in which the substrate 10 is circular.

According to this reference example, the reduction of sensitivity caused by displacement can be suppressed as compared with a case where the substrate 10 is circular and the support body 30 is circularly annular. Therefore, even when the mounting position of the fluid pressure detection device is limited, the reduction of sensitivity can be suppressed. When the longitudinal direction of the piezoelectric element 20 is parallel to the short-length direction of the substrate 10 as in the first constitution example, sensitivity can be further improved as compared with a case where the substrate 10 is circular.

Figure 30:
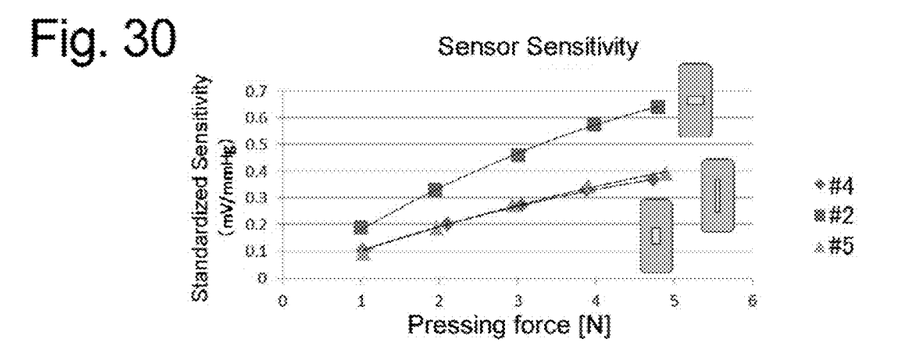
FIG. 30 is a graph showing the relationship between pressing force and standardized sensitivity according to the shape of the piezoelectric element 20 in the fluid pressure detection devices of the second reference example.

FIG. 30 is a graph showing the relationship between pressing force and standardized sensitivity according to the shape of the piezoelectric element 20 in the fluid pressure detection devices of the second reference example. #5 represents an example in which the size of the piezoelectric element 20 is 1 mm×8 mm in the second constitution example of this reference example. It was found from FIG. 30 that the standardized sensitivity of the constitution of #2 was the highest. Therefore, in an embodiment which will be described hereinafter, further improvement will be made based on the constitution of #2.

Embodiment

Figure 31A:
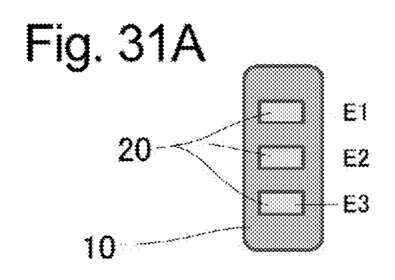
FIG. 31A is a plane view of a first constitution example and FIG. 31B is a plane view of a second constitution example.
Figure 31B:
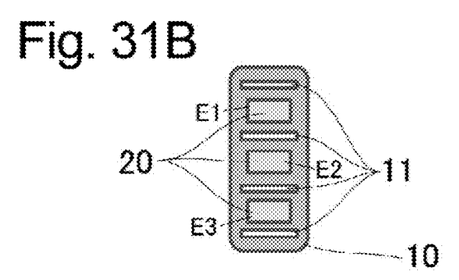

FIG. 31A and FIG. 31B are plane views of the substrate 10 and the piezoelectric elements 20 of a fluid pressure detection device according to an embodiment of the present invention. FIG. 31A shows a first constitution example and FIG. 31B shows a second constitution example. The first constitution example of this embodiment is the same as the first constitution example (FIG. 26A) of the second reference example except that three piezoelectric elements 20 are arranged (arrayed) in the longitudinal direction of the substrate 10. The second constitution example of this embodiment is the same as the first constitution example except that the substrate 10 has slits 11 on both sides in the short-length direction of each piezoelectric element 20. The slits 11 are parallel to the longitudinal directions of the piezoelectric elements 20. To distinguish the three piezoelectric elements 20 from one another, they are represented by E1, E2 and E3 from top in the figure. The I-V conversion circuit shown in FIG. 11 and the integrating circuit shown in FIG. 13 are provided for each piezoelectric element 20.

Figure 32A:
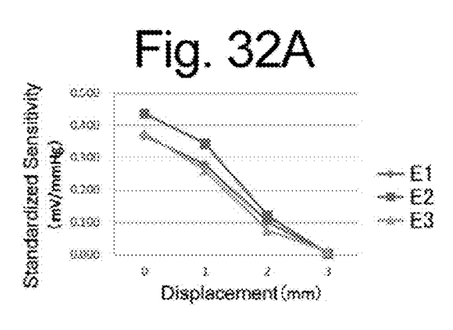
FIG. 32A is a graph showing the first constitution example and FIG. 32B is a graph showing the second constitution example.
Figure 32B:
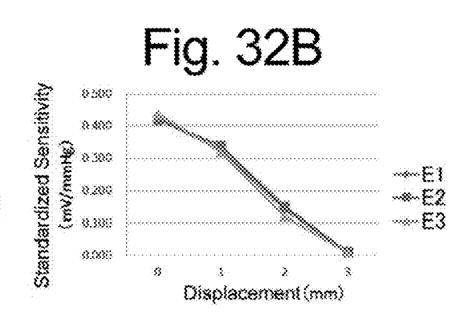
Figure 33A:
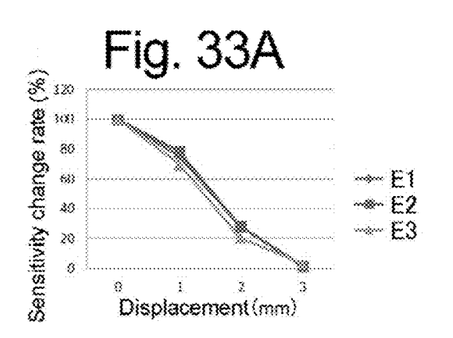
FIG. 33A is a graph showing the first constitution example and FIG. 33B is a graph showing the second constitution example.
Figure 33B:
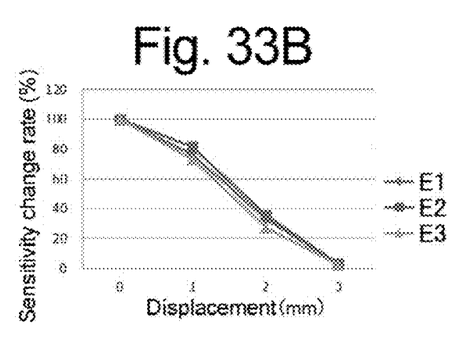

FIG. 32A and FIG. 32B are graphs showing the relationship between the displacement against the tube 7 and standardized sensitivity in the fluid pressure detection device of the embodiment. FIG. 32A shows the first constitution example and FIG. 32B shows the second constitution example. FIG. 33A and FIG. 33B are graphs showing the relationship between the displacement against the tube 7 and sensitivity change rate in the fluid pressure detection device of the embodiment. FIG. 33A shows the first constitution example and FIG. 33B shows the second constitution example. It was found from comparison between FIG. 32A and FIG. 32B and comparison between FIG. 33A and FIG. 33B that the reduction of sensitivity caused by a displacement amount of not more than 2 mm is suppressed when the substrate 10 has the slits 11.

Figure 34:
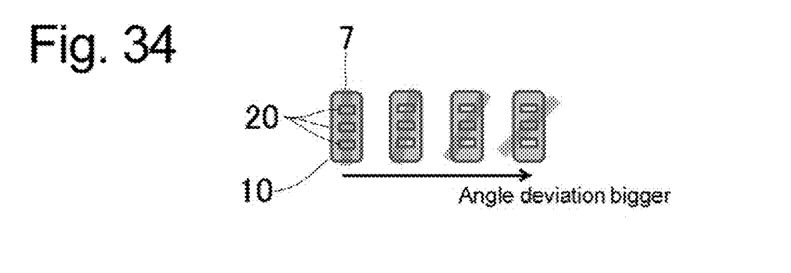
FIG. 34 is a diagram for explaining the angle deviation between the substrate 10 and the tube 7.

FIG. 34 is a diagram for explaining the angle deviation between the substrate 10 and the tube 7. The angle deviation to be studied hereinafter is an angle at which the extending direction of the tube 7 turns relative to the longitudinal direction of the substrate 10 while the tube 7 passes the center of the substrate 10 as shown in FIG. 34. 0° means that the extending direction of the tube 7 is parallel to the longitudinal direction of the substrate 10.

Figure 35A:
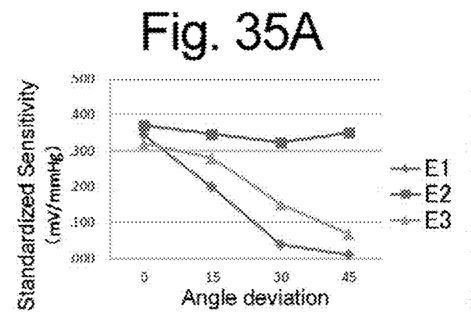
FIG. 35A is a graph showing the first constitution example and FIG. 35B is a graph showing the second constitution example.
Figure 35B:
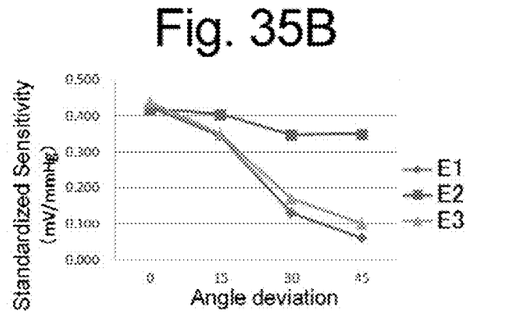
Figure 36A:
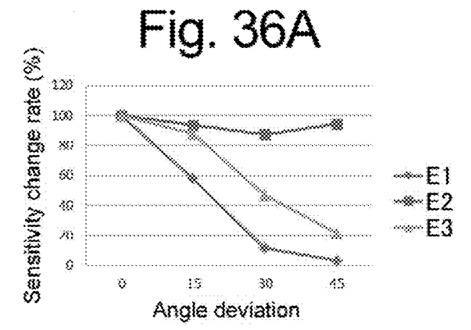
FIG. 36A is a graph showing the first constitution example and FIG. 36B is a graph showing the second constitution example.
Figure 36B:
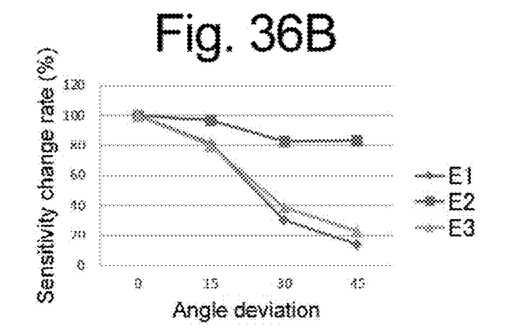
Figure 37A:
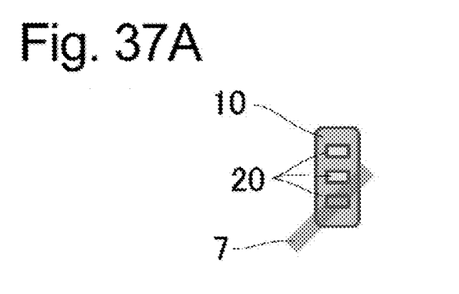
FIG. 37A and FIG. 37B are explanation diagrams showing that the deviation of an angle between the substrate 10 and the tube 7 and displacement therebetween are combined.
Figure 37B:
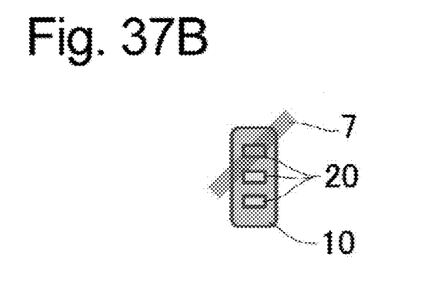

FIG. 35A and FIG. 35B are graphs showing the relationship between the angle deviation against the tube 7 and standardized sensitivity in the fluid pressure detection device of the embodiment. FIG. 35A shows the first constitution example and FIG. 35B shows the second constitution example. FIG. 36A and FIG. 36B are graphs showing the relationship between the angle deviation against the tube 7 and sensitivity change rate in the fluid pressure detection device of the embodiment. FIG. 36A shows the first constitution example and FIG. 36B shows the second constitution example. As shown in the graphs, it was found that, even when an angle deviation occurs, the central piezoelectric element 20 can maintain a high sensitivity of not less than 80% as compared with a case where there is no angle deviation. When a certain amount of displacement is added to an angle deviation as shown in FIG. 37A and FIG. 37B, one of the piezoelectric elements 20 except the central piezoelectric element 20 can maintain high sensitivity. Stated more specifically, in the case of FIG. 37A, a lower piezoelectric element 20 in the figure maintains high sensitivity. In the case of FIG. 37B, an upper piezoelectric element 20 in the figure maintains high sensitivity.

According to this embodiment, the reduction of sensitivity caused by the angle deviation (and a combination of angle deviation and displacement) of the tube 7 can be suppressed by arraying the piezoelectric elements 20. Also, the reduction of sensitivity caused by the displacement of the tube 7 can be suppressed by forming the slits 11 as in the second constitution example. The number of the piezoelectric elements 20 is not limited to three and may be 2, or 4 or more. The piezoelectric elements 20 may be arranged in a matrix in the longitudinal direction and short-length direction of the substrate 10 or in two arbitrary directions of the substrate 10. The presence of the support body 30 provides an advantage in the reproducibility of pressure detection. However, even without the support body 30, the reduction of sensitivity caused by the angle deviation (and a combination of angle deviation and displacement) of the tube 7 can be suppressed as compared with the case where there is only one piezoelectric element 20. And, even without the support body 30, the reduction of sensitivity caused by the displacement of the tube 7 can be suppressed as compared with the case where there is no slit 11. If a configuration wherein an external pressing member presses only a part, which is supported by the support body 30, of the base material 10, the reproducibility of pressure detection of the fluid pressure detection device can be improved even without the support body 30 as same as the support body 30 is provided.

While the invention has been described in its preferred embodiments, it is to be understood by a person having ordinary skill in the art that variations may be made on each constituent element and process of the embodiments without departing from the scope of the following claims. Variations of the invention will be described hereinafter.

The substrate 10, the support body 30 and the lid body 40 may be insulators made of a resin or the like. The support body 30 is not limited to a single annular member. A plurality of support bodies 30 may be provided on both sides of or around the piezoelectric elements 20. Specific numerical values (sizes of the substrate 10 and the piezoelectric elements 20, pressing force, etc.) shown in above embodiments are just examples and may be suitably changed according to required specifications.

EXPLANATIONS OF LETTERS OF NUMERALS 1 fluid pressure detection device, 5 human body, 6 fluid, 7 tube, 7a human skin gel, 8 tube holder, 9 force gauge, 10 substrate (diaphragm), 11 slit, 20 piezoelectric element, 30 support body, 31 notch, 32 stepped part, 33, 34 recessed part, 40 lid body, 41 through hole, 50 terminal part, 60 cable, 70 pressing member, 81 frame body, 82 round wire coil spring, 83 cap.

The invention claimed is:

1. A fluid pressure detection device, for detecting pressure of a fluid flowing inside a tube, comprising:
a substrate having first and second surfaces; and
a plurality of piezoelectric elements on the first surface of the substrate, wherein
the tube is deformed with deformation of the second surface of the substrate,
the substrate has a substantially rectangular shape with longer sides and shorter sides,
the piezoelectric elements are arranged along a longitudinal direction of the substrate with longer sides of each of the piezoelectric elements being substantially perpendicular to the longer sides of the substrate, and
the substrate has slits on both sides of each of the piezoelectric elements in the longitudinal direction of the substrate.

2. The fluid pressure detection device according to claim 1, comprising a pressing member for pressing the substrate from the first surface to press the second surface of the substrate against the tube.

3. The fluid pressure detection device according to claim 2, wherein the pressing member applies a pressure of not less than 40 mmHg from the first surface of the substrate.

4. A fluid pressure detection device for detecting pressure of a fluid flowing inside a tube, comprising:
a substrate having first and second surfaces; and
a plurality of piezoelectric elements on the first surface of the substrate, wherein
the tube is deformed with deformation of the second surface of the substrate,
the substrate has a substantially rectangular shape with longer sides and shorter sides,
the piezoelectric elements are arranged along a longitudinal direction of the substrate with longer sides of each of the piezoelectric elements being substantially perpendicular to the longer sides of the substrate, the longer sides of the substrate are substantially parallel to a direction in which the tube extends, and the substrate has slits on both sides of each of the piezoelectric elements in the longitudinal direction of the substrate.

5. The fluid pressure detection device according to claim 4, comprising a pressing member for pressing the substrate from the first surface to press the second surface of the substrate against the tube.

6. The fluid pressure detection device according to claim 5, wherein the pressing member applies a pressure of not less than 40 mmHg from the first surface of the substrate.

* * * * *